United States Patent [19]
Davis

[11] Patent Number: 5,424,142
[45] Date of Patent: Jun. 13, 1995

[54] NEGATIVE CONTRAST AGENTS FOR MAGNETIC RESONANCE IMAGING COMPRISING BARIUM SULFATE AND A CLAY

[75] Inventor: Michael A. Davis, Westwood, Mass.
[73] Assignee: E-Z-EM, Inc., Westbury, N.Y.
[21] Appl. No.: 65,192
[22] Filed: May 20, 1993
[51] Int. Cl.6 ............................................. A61B 5/055
[52] U.S. Cl. ................................. 424/9.31; 436/173; 424/684; 424/709
[58] Field of Search ...................... 424/9, 4, 709, 684; 436/173; 128/653.4, 654

[56] References Cited
U.S. PATENT DOCUMENTS

| | | | |
|---|---|---|---|
| 4,010,038 | 3/1977 | Iwasaki et al. | 106/22 |
| 4,126,672 | 11/1978 | Sheth et al. | 424/22 |
| 4,916,170 | 4/1990 | Nambu et al. | 523/137 |
| 5,205,290 | 4/1993 | Unger | 128/653.4 |
| 5,277,896 | 1/1994 | Balkus, Jr. | 424/9 |

Primary Examiner—Gary E. Hollinden
Attorney, Agent, or Firm—Fisher McAulay Nissen Goldberg & Kiel

[57] ABSTRACT

A negative contrast agent for MRI is an aqueous suspension having a quantity of barium sulfate between 25 and 30 percent by weight and a quantity of bentonite between 2.5 and 3.5 percent by weight and between 0.15 and 0.25 mM Fe as a ferrite. Such a negative contrast agent provides substantially black imaging in a T2 weighted pulse sequence; namely a relative signal intensity (RSI) of near zero. It also provides a relative signal intensity (RSI) of well under 10 percent of that of water in a T1 weighted pulse sequence.

10 Claims, 2 Drawing Sheets

Relative Signal Intensity of BaSO4 - Bentonite- Fe Mixtures

TABLE I    FIG.2

| COMPOSITION | RSI (SE400/20)* |
|---|---|
| 2.5% Bentonite + 0.16 mM Fe + 20% Barium | 0.119 |
| "          "          + 30% Barium | 0.039 |
| "          "          + 40% Barium | 0.002 |
| "          "          + 50% Barium | 0.002 |
| 3.0% Bentonite + 0.16 mM Fe + 15% Barium | 0.157 |
| "          "          +20% Barium | 0.099 |
| "          "          +30% Barium | 0.039 |
| "          "          +40% Barium | 0.010 |

* These are all points on the curve 14 in FIG. 1. Curve 14 is actually two curves. But the resolution of FIG. 1 does not distinguish between the two curves.

FIG.3

TABLE II

| MATERIAL | RSI (T2) | RSI (T1) |
|---|---|---|
| 25% $BaSO_4$ | 0.285 | 0.793 |
| 3% Bentonite | .004 | 0.800 |
| 0.16 mM Fe | 0.569 | 1.880 |
| 25% $BaSO_4$ + 3% Bentonite | - 0 - | 0.220 |
| 25% $BaSO_4$ + 0.16 mM Fe | 0.79 | 1.510 |
| 3% Bentonite + 0.16 mM Fe | .002 | 0.540 |
| 25% $BaSO_4$ + 3% Bentonite + 0.16 mM Fe | - 0 - | 0.099 |

NEGATIVE CONTRAST AGENTS FOR MAGNETIC RESONANCE IMAGING COMPRISING BARIUM SULFATE AND A CLAY

BACKGROUND OF THE INVENTION

This invention relates in general to an improved formulation for a negative contrast agent adapted to be used with magnetic resonance imaging (MRI) and more particularly to agents that can be employed in the gastrointestinal (GI) track.

The use of contrast agents for MRI and, in particular, use of negative oral contrast agents for GI track identification in MRI are well known. Among the many agents that are known are those that are disclosed in U.S. Pats. No. 4,927,624 (the use of clay); 4,770,183 (the use of a particular size superparamagnetic metal oxide particles) and 5,069,216 (biologically degradable superparamagnetic metal oxides having less than a predetermined average diameter).

In general, applicant understands that the primary uses and investigation has focused on perflurocarbons and ferrite materials. Although these materials are effective in providing a good contrast, they are relatively expensive and they pose problems of toxicity.

Barium sulfate (barium) has been tried on at least an experimental basis as have various clays including, most significantly, bentonite. With a concentration of these materials that is acceptable to the patient, the contrast improvement is very limited. In order to get an optimum contrast improvement, the amount and concentration of barium or clay material required is unacceptable. It is not only difficult to ingest but causes an unacceptable amount of constipation.

Accordingly, it is a major purpose of this invention to provide an improved formulation for a negative image contrast agent for use with MRI that will avoid the previously known toxicity, palatability and constipation problems that occur with presently known agents.

It is another related purpose of this invention to provide the above object with an agent that has reasonable cost so as to facilitate its use in as wide a variety of applications as possible.

The U.S. Pat. No. 5,069,216, issued Dec. 3, 1991 provides a fairly extensive discussion of the technology in this art and need not be repeated here. The agents of concern are called negative contrast agents because they serve to decrease the signal intensity thereby resulting in image darkening. More particularly, in MRI, the images are produced on the trailing edge of a magnetic pulse when the hydrogen nuclei in tissue provide a signal when switching from a magnetized to a demagnetized state. The switch is called a relaxation switch and the time it takes is called a relaxation time period. Without going into the specific physics of it, there are two relaxation times, called T1 and T2 (respectively longitudinal relaxation time and transverse relaxation time). These two relaxation times T1 and T2 generate two different signals which provide two different images.

Indeed, every pulse sequence generates both T1 and T2 signals in a specific proportion. Those sequences generating substantially more T1 signal are referred to herein as T1 weighted pulse sequences which yield T1 weighted images. The converse applies with respect to those sequences generating a substantially larger T2 signal which yield T2 weighted images.

The image produced often lacks clear definition (contrast) because of comparable signals produced by adjacent tissues other than the organ or tissue of interest. That contrast agent which localizes or concentrates in a tissue serves to modify the magnetic properties of that tissue in which it concentrates and thus can provide a better contrast between that tissue and the surrounding tissue.

Negative contrast agents operate in three different ways to modify the magnetic properties of the tissue in which they are concentrated. These three ways are the following:

A. By increasing the magnetic susceptibility of the tissue. Superparamagnetic agents operate in this way and to a much lesser extent so does barium and clay.

B. By decreasing proton density. This occurs by displacing water. This is how barium, perfluorocarbons and gas work.

C. By reducing the rotational mobility of the protons present. This is essentially how the clays work.

It is important to recognize that an optimum contrast agent is one which will provide an appropriate trade-off of three functional characteristics. These three functional characteristics are: (1) provides a marked contrast between the tissue of interest and the surrounding tissue, (2) has minimum adverse medical impact on the patient; and (3) is as acceptable as possible to a patient from the point of view of taste and comfort. An optimum contrast agent is one that does not hold its magnetic state in the absence of an employed magnetic field, is not toxic to the human body and does not require quantities which will cause discomfort such as constipation.

In addition, cost is a major factor in providing an agent which is to be used in a large number of procedures. Thus it is another object of this invention to obtain an optimum trade-off of the above three functional characteristics together with cost as a fourth parameter.

DEFINITIONS

Relaxation Time

This is the time, usually in fractions of a second, in which the hydrogen nucleus switches from a magnetized state to a demagnetized state when the magnetic pulse is removed. There is a different relaxation time for the T1 mode and for the T2 mode. The relaxation time in the T1 mode can be as little as 2.2 seconds for a 40 percent by weight of barium sulfate and as little as 0.12 seconds in the T1 mode for 4% by weight of bentonite. The relaxation time in the T2 mode can range from 0.4 seconds for a 10 percent barium sulfate solution to 0.05 seconds for a 5 percent bentonite solution. Relaxation time has a significant relationship to the signal intensity. However, that relationship is quite complex.

T1 Weighted And T2 Weighted Modes

This terminology is known in the art and will not be explicated in detail here because of its complexity. This disclosure indicates the particular pulse sequence that was used in the T1 mode and T2 mode. Specifically, a known pulse sequence that is designated in the art as SE400/20 is a pulse sequence used for the T1 weighted mode and a known pulse sequence SE1500/50 was employed when testing response in the T2 weighted mode.

Relative Signal Intensity (RSI)

The signal intensity of water is deemed to be 1.0. The signal intensity of various substances, barium sulfate, bentonite or ferrite are measured relative to water. The materials considered as a negative contrast agent provide a signal intensity response substantially less than that of water and thus can be compared with water by designating what fraction of signal intensity they provide compared to that of water. Thus relative signal intensity for a negative contrast agent is less than 1.0. In the case of certain barium sulfate compositions, the RSI can be greater than 1.0. But RSI is the key figure of merit for measuring the negative contrast agents. The lower the RSI, the better the negative contrast. It should be noted that the RSI has to be measured in response to both the T1 weighted signal as well as in response to the T2 weighted signal.

Barium In this field, barium sulfate ($BaSO_4$) is often referred to as barium. That convention will be frequently followed herein and any reference to "barium" should be understood to mean barium sulfate.

The following terms are used herein to designate materials having the indicated properties.

A broad distinction is the distinction between Diamagnetic and Paramagnetic materials. All materials (including liquids and gases) are either Diamagnetic or Paramagnetic. This division refers to the direction of magnetization of the material when subjected to a magnetic field. In particular:

Diamagnetic materials have a magnetization that is anti-parallel with the applied field.

Paramagnetic materials have a magnetization that is parallel with the applied field.

Paramagnetic materials can be divided into Ferrimagnetic and Ferromagnetic materials.

Ferromagnetic materials are Paramagnetic materials which exhibit significant hysteresis. Essentially, iron, nickel, cobalt and certain alloys which contain those elements constitute most if not all ferromagnetic materials.

These ferromagnetic materials not only have hysteresis but also tend to have fairly high susceptibility. That is, the magnetization induced by an applied field tends to be fairly great. The magnetization is linear at first and then saturates. The application of an alternating applied field will generate a hystereis. All ferromagnetic materials can form permanent magnets. That is a function of the hysteresis loop.

Ferrimagnetic materials are Paramagnetic materials which do not form a hysteresis loop. Accordingly, they do not form permanent magnets. Many Ferrimagnetic materials have low susceptibility. That is, the magnetization generated by an applied field of a given strength is much less than occurs when that same magnetic field is applied to a Ferromagnetic material. However, there are exceptions. These exceptions are called Superparamagnetic materials.

Superparamagnetic materials are high susceptibility Ferrimagnetic materials which provide large magnetization (generally less than that of Ferromagnetic materials) but which do not have hysteresis and thus do not have permanent magnetization. Because of the contrast between Superparamagnetic and Ferromagnetic materials, there is a tendency to think that Ferromagnetic materials are not Paramagnetic. But Ferromagnetic materials are Paramagnetic. It is just that the term Superparamagnetic has grown to be the term applied to Ferrimagnetic materials that have high susceptibility. These Superparamagnetic materials have a magnetization curve which is at first linear and then saturates. When the field is removed, the magnetization curve retraces its contour back to zero rather than create a hystereis curve.

BRIEF DESCRIPTION OF THE DRAWINGS

FIG. 2 provides a table designated as Table I which provides the specific data from which curve 14 of FIG. 1 is plotted. The RSI numbers in Table I are taken from lab measurements. The standard deviation is appreciable so that an RSI measurement of 0.002 has a measurement error that makes it comparable to the 0.010 measurement. The numbers represent present measurements and will require refinement. The resultant curves indicate tendencies and direction.

FIG. 3 provides a table designated as Table II which is a table contrasting RSI responses in T1 and T2 weighted modes of various compositions. Table II provides a comparison of RSI response for individual constituents and for mixtures of this invention.

BRIEF DESCRIPTION OF THE INVENTION

Figure 1:
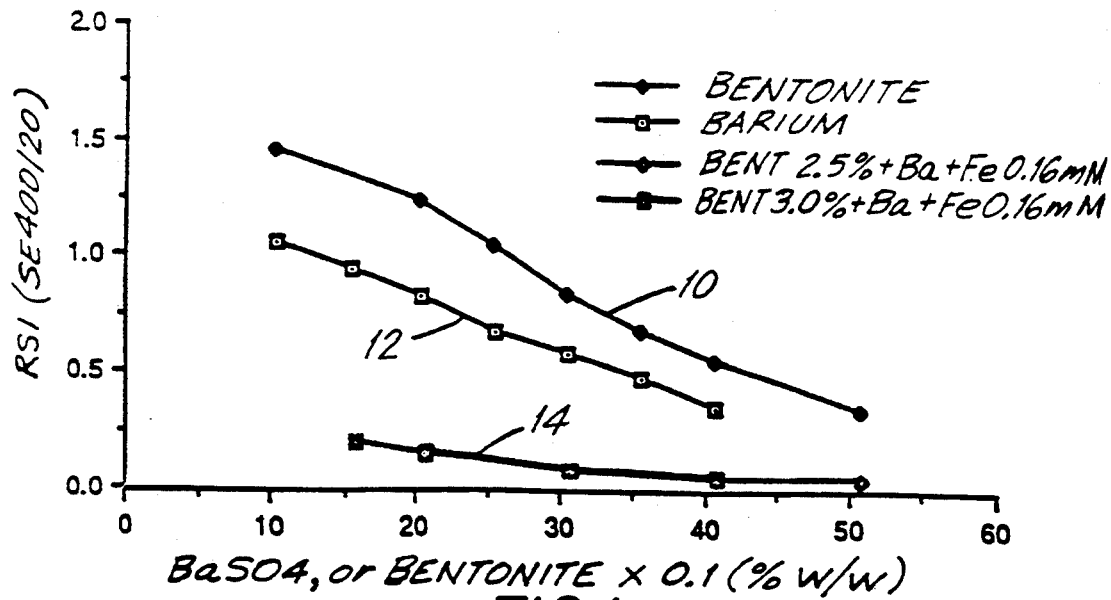
FIG. 1 is a graph showing the relative signal intensity (RSI) in response to a typical T1 weighted pulse sequence for barium (curve 10) bentonite (curve 12) and two preferred compositions (curve 14) of this invention.

What applicant has determined is that particular combinations of known negative contrast agents provide an enhanced result which permits the use of sufficiently smaller amounts of the constituents so as to meet the objectives of this invention.

More particularly, an amount of barium sulfate (barium) acceptable to the patient containing a relatively small percentage of a ferrite or bentonite or a combination of a ferrite and bentonite provides an effective darkening (negative) contrast agent in both T1 and T2 weighted images. The barium concentration required is approximately half of that required without the second constituent.

One fairly optimum formulation, based on non-human testing, is an aqueous suspension having 25 to 30 percent by weight of barium sulfate, 2.5 to 3.0 percent by weight of bentonite and 0.2 to 0.25 millimolar (mM) of the iron constituent as a ferrite.

However, it is believed that a range of barium from 20 to 50 percent by weight can be useful with bentonite having a range of between 2.0 and 4.0 percent by weight and ferrite between 0.15 and 1.5 mM.

DESCRIPTION OF THE PREFERRED EMBODIMENTS

A preferred embodiment of this invention employs a mixture of barium sulfate, bentonite and ferrite in a water medium.

It has been found that by using over two percent of bentonite, the RSI of a T2 weighted signal can be reduced to essentially zero.

However, as shown in FIG. 1, use of 2.5 percent to 3.0 percent of bentonite will reduce the RSI of a T1 weighted signal to only 0.5; that is to fifty percent of the signal produced by water.

FIG. 1 is an instructive curve to illustrate the relative signal intensity (RSI) for a very typical T1 pulse sequence SE400/20 for bentonite, curve 10; barium, curve 12 and two formulations of this invention, curve 14. The two formulations produce overlapping curves. Table I, associated with FIG. 1, lists the values experimentally obtained that are used to generate the curve 14.

More particularly, curve 10 shows that the RSI for bentonite ranges from 1.5 where the Bentonite concentration is one percent by weight to approximately 0.35 when the bentonite is five percent by weight in a water carrier. The numbers on the X-axis in FIG. 1 have to be divided by ten to provide the bentonite weight percent values.

Curve 12 shows that for barium sulfate, the RSI ranges from approximately 1.0 at a ten percent by weight of barium in a water carrier to an RSI of approximately 0.35 with a forty percent by weight of barium.

Curve 14 shows that when bentonite is anywhere between 2.5 percent to 3.0 percent by weight and ferrites are at 0.16 millimolar (mM) then the RSI ranges from approximately 0.16 at fifteen percent by weight of barium to approximately 0.002 when barium is as high as fifty percent by weight.

Because the higher values of barium are not acceptable to a patient, the preferred embodiment will employ barium somewhere between twenty-five and thirty percent by weight.

It should be noted that FIG. 1 illustrates RSI for the T1 mode. When bentonite is over two percent by weight, the RSI for the T2 mode is essentially zero. It should be noted that the ferrite at 0.16 millimolar (mM) by itself provides an RSI of close to two; meaning that the signal it would generate would be twice as strong as that of water.

As shown in Table II, the three percent level of bentonite effectively eliminates all T2 mode signal in all combinations. However, the RSI for the T1 mode is as high as 80 percent (0.8) with a twenty-five percent barium composition and as high as 80 percent with a three percent bentonite composition. Combining twenty-five percent barium and three percent bentonite provides an RSI for the T1 mode of about twenty percent (0.2). It should be noted that 0.16 millimolar (mM) ferrite substantially greater than that of water. Combining that amount of ferrite with barium increases the RSI from 80 percent to 150 percent. Combining that amount of ferrite with bentonite decreases the RSI modestly from 80 percent to 60 percent.

But, combining that amount of ferrite with the barium and bentonite combination cuts the RSI in half from 20 percent to 10 percent. This substantial reduction of RSI when all three elements are combined provides a significant result for a negative contrast agent.

The RSI results shown in Table II show that 0.16 mM ferrite has a substantial RSI by itself and indeed when added to barium or bentonite will either increase the total or change it very little. Yet, it has been found that a larger quantity of ferrite will have the effect of reducing the RSI in the T1 mode quite substantially. For example, if the amount of ferrite is 1.0 mM, the RSI for the T1 mode can be reduced to essentially zero. However, because of the cost factor this amount of ferrite is impractical. However, the ferrite can be reduced substantially to approximately 0.5 mM or less when in combination with appropriate amounts of barium and bentonite to provide an RSI even less than that of the last line on Table II.

The ferrite employed is a commercially available material that has as its major constituent $Fe_3O_4$ and includes other components such as $Fe_2O_3$. These ferrites are paramagnetic materials which do not form a hysteresis loop and thus are ferrimagnetic materials. Their high susceptibility means that they are specifically superparamagnetic materials.

A number of different barium sulfate compositions have been tested to determine the different effects they have on RSI. Commercially available barium compositions have an RSI in the T1 weighted mode that range from approximately 0.3 to over 1.0. It is not understood as to what it is about these commercially available barium sulfate constituents that affects their response in the T1 weighted mode. A suggestion that it is particle size has been made and various examinations of the compositions show no relationship between particle size and RSI. Comparative tests of various barium compositions were made with a barium concentration of a bit under 50 percent.

High density barium such as the barium sold as Liquid HD by E-Z-EM, Inc. of 717 Main Street, Westbury, N.Y. appear to work best to provide a low RSI in T1 mode. In general, some variation in the constituents; barium, bentonite and ferrite, should be tested and selected as a function of the desired trade-off of cost, patient acceptability, side-effect and image clarity parameters.

What is claimed is:

1. A negative contrast agent used in magnetic resonance imaging of the gastrointestinal tract comprising:
   a suspension having a substantial portion of a first constituent consisting of barium sulfate and a second constituent comprising at least one of the group of agents consisting of clay, said second constituent constituting at least two percent by weight of said suspension.

2. The negative contrast agent of claim 1 wherein said second constituent is bentonite.

3. The negative contrast agent of claim 1 wherein said suspension is a water base suspension.

4. The negative contrast agent of claim 2 wherein said suspension is a water base suspension.

5. The negative contrast agent of claim 4 wherein:
   said barium sulfate is between 25 percent and 30 percent by weight of said suspension and said bentonite is between 2.5 percent and 3.5 percent by weight of said suspension.

6. The negative contrast agent of claim 3 wherein:
   said barium sulfate is between 25 percent and 30 percent by weight of said suspension and said bentonite is between 2.5 percent and 3.5 percent by weight of said suspension.

7. The negative contrast agent of claim 1 wherein the quantity by weight of said clay is substantially less than the quantity by weight of said barium sulfate.

8. The negative contrast agent of claim 2 wherein the quantity by weight of said bentonite is substantially less than the quantity by weight of said barium sulfate.

9. The negative contrast agent of claim 2 wherein:
   said barium sulfate is between 20 percent and percent by weight of said suspension and said bentonite is between 2.0 percent and 4.0 percent by weight of said suspension.

10. The negative contrast agent of claim 4 wherein:
    said barium sulfate is between 20 percent and 50 percent by weight of said suspension and said bentonite is between 2.0 percent and 4.0 percent by weight of said suspension.

* * * * *